United States Patent
Lu et al.

(10) Patent No.: US 10,496,160 B2
(45) Date of Patent: Dec. 3, 2019

(54) GAZE TRACKING SYSTEM WITH CALIBRATION IMPROVEMENT, ACCURACY COMPENSATION, AND GAZE LOCALIZATION SMOOTHING

(71) Applicant: KONINKLIJKE PHILIPS N.V., Eindhoven (NL)

(72) Inventors: Kongkuo Lu, Briarcliff Manor, NY (US); Yuechen Qian, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/535,747

(22) PCT Filed: Dec. 7, 2015

(86) PCT No.: PCT/IB2015/059390
§ 371 (c)(1),
(2) Date: Jun. 14, 2017

(87) PCT Pub. No.: WO2016/097919
PCT Pub. Date: Jun. 23, 2016

(65) Prior Publication Data
US 2017/0364149 A1  Dec. 21, 2017

Related U.S. Application Data

(60) Provisional application No. 62/092,349, filed on Dec. 16, 2014.

(51) Int. Cl.
*G06F 3/01* (2006.01)
*A61B 3/113* (2006.01)

(52) U.S. Cl.
CPC .............. *G06F 3/013* (2013.01); *A61B 3/113* (2013.01)

(58) Field of Classification Search
CPC ....................................... G06F 3/013
See application file for complete search history.

(56) References Cited

U.S. PATENT DOCUMENTS

| | | |
|---|---|---|
| 5,913,079 A | 6/1999 | Aoyama et al. |
| 6,152,563 A | 11/2000 | Hutchinson et al. |
| 6,421,064 B1 | 7/2002 | Lemelson et al. |
| 2009/0268045 A1 | 10/2009 | Sur |
| 2011/0069277 A1 | 3/2011 | Blixt et al. |
| 2013/0002846 A1 | 1/2013 | De Bruijn et al. |

(Continued)

*Primary Examiner* — Dennis P Joseph (57) ABSTRACT

In a gaze-tracking system, localized error correction may be applied. The display area may be partitioned into error-correction zones, and each zone may have its own error correcting parameters or function. Calibration points may be defined for each of these zones, and the correction parameters or function within each zone may be dependent upon the observed errors as the user views each calibration point associated with the zone. In like manner, the function applied to smooth the determined gaze point to reduce noise may also be localized by basing its characteristics on the noise exhibited at each calibration point associated with defined noise-calibration zones. The error correcting function and/or the noise smoothing function may be selected based on the requirements of the particular application that receives the corrected and smoothed gaze location.

20 Claims, 8 Drawing Sheets

(56) References Cited

U.S. PATENT DOCUMENTS

| | | |
|---|---|---|
| 2013/0235347 A1 | 9/2013 | Hennessey et al. |
| 2014/0160005 A1 | 6/2014 | Lee et al. |
| 2014/0268055 A1 | 9/2014 | Skogo et al. |
| 2015/0199812 A1* | 7/2015 | Hakoshima ............ A61B 3/113 348/78 |
| 2016/0005176 A1* | 1/2016 | Nguyen .................. G06F 3/013 382/103 |
| 2016/0048964 A1* | 2/2016 | Kruglick ............... G06T 7/0044 345/633 |

* cited by examiner

GAZE TRACKING SYSTEM WITH CALIBRATION IMPROVEMENT, ACCURACY COMPENSATION, AND GAZE LOCALIZATION SMOOTHING

CROSS-REFERENCE TO PRIOR APPLICATIONS

This application is the U.S. National Phase application under 35 U.S.C. § 371 of International Application No. PCT/IB2015/059390, filed on Dec. 7, 2015, which claims the benefit of U.S. Provisional Application No. 62/092,349, filed on Dec. 16, 2014. These applications are hereby incorporated by reference herein.

FIELD OF THE INVENTION

This invention relates to the field of gaze tracking, and in particular to a system and method that provides an improved calibration process, local accuracy compensation, and local gaze smoothing.

BACKGROUND OF THE INVENTION

The use of gaze tracking to control the selection of options on a display device, or the identification of objects of interest in a displayed image, continues to increase, particularly in view of the availability of low-cost gaze tracking devices and software, such as offered by Tobii Technology, Inc. and The Eye Tribe.

Gaze tracking may also be used in a 'passive' mode, wherein a user's gazing pattern is monitored to determine the user's reaction to image composition, such as the arrangement of elements on a web-page, a gaming program, and so on. Passive monitoring may also be used for physiological research, such as determining how different people react to different simulated vehicular situations. In like manner, passive monitoring may be implemented in a vehicle to issue an alert if the driver's gaze is abnormal.

In a conventional gaze tracking device, the angular deviation from 'straight ahead' is measured, using optical devices, including cameras and infrared emitters and receivers, or other devices, such as devices that measure biometric parameters. Example gaze tracking devices and their application may be found at USPA 2011/0069277, "VISUAL DISPLAY WITH ILLUMINATORS FOR GAZE TRACKING", filed Mar. 24, 2011 for Blixt et al.; USPA 2014/0268055, "EYE/GAZE TRACKER AND METHOD OF TRACKING THE POSITION OF AN EYE AND/OR A GAZE POINT OF A SUBJECT", filed Mar. 7, 2014 for Skogo et al.; USPA 2013/0235347, "SYSTEM AND METHOD FOR INTERACTING WITH AND ANALYZING MEDIA ON A DISPLAY USING EYE GAZE TRACKING", filed Apr. 25, 2013 for Hennessey et al.; USPA 2009/0268045, "APPARATUS AND METHODS FOR CONFIGURATION AND OPTIMIZATION OF IMAGE SENSORS FOR GAZE TRACKING APPLICATIONS", filed Aug. 4, 2008 for Sur et al.; USPA 2013/0002846, "SYSTEM AND METHOD FOR TRACKING THE POINT OF GAZE OF AN OBSERVER", filed Mar. 15, 2011 for Frederick Jan De Bruijn, Karl Catherine Van Bree, and Tommaso Gritti; and USPA 2014/0160005, "APPARATUS AND METHOD FOR CONTROLLING GAZE TRACKING", filed May 7, 2013 for Lee et al. Each of these cited publications are incorporated by reference herein.

To accurately map a user's gaze to a location on a display screen, gaze tracking devices determine and apply a calibration procedure to compensate for the optical characteristics of each user. This calibration may be active, wherein, for example, the user is directed to gaze at particular points on the display screen, or passive, wherein, for example, the device provides stimuli from a known location while the user is viewing the display device, and detects the angle at which the stimuli strikes the user's eye(s).

Figure 1:
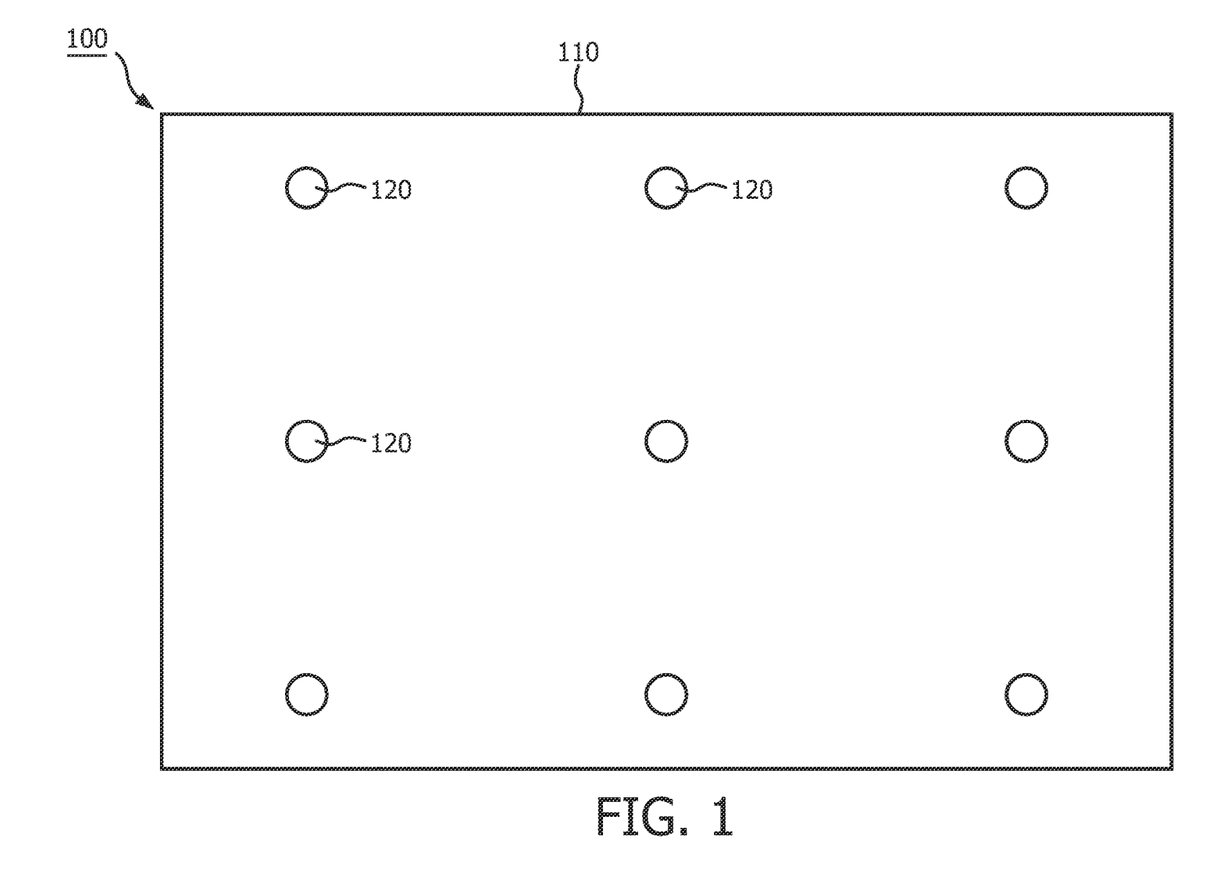
FIG. 1 illustrates an example calibration display used by a conventional gaze tracking device.

FIG. 1 illustrates an example illumination pattern 100 that may be used during an active calibration, such as used in a device provided by The Eye Tribe. The pattern comprises a dark background 110 with nine selectable illumination points 120, or 'targets'. The calibration element of the device selectively illuminates one of the illumination points and detects the angle(s) of the user's eye(s) as the user gazes at the illuminated point. The example calibration element determines, based on the location of the user's eyes relative to the display device and 3-D geometry, the 'true' angles of each illumination point from the user's eyes. The difference between each measured ('actual') angle of the user's eyes when observing the illumination point and the 'true' angle of the illumination point from the user's eye defines the 'error' factor for this particular user.

Any of a variety of techniques may be used to determine a correction function to be applied to the 'actual' angles that will minimize the errors between the 'corrected' angle and the 'true' angle. In an example embodiment, a linear correction function that minimizes the sum of the squares of the errors is determined that includes an offset and a scaling factor that is applied to the 'actual' angles. Non-linear correction functions may also be used, such as a second order function that minimizes the errors.

A limitation of the use of a correction function is that it assumes a certain 'uniformity' in the errors that can be modeled with a single correction function. That is, for example, using a linear correction function assumes that the errors exhibit a linear variation across the display; a second order correction function assumes that the errors exhibit a pattern that corresponds to a second order (quadratic) effect.

Conventional correction functions are generally included within the gaze tracking software provided by the provider/developer, because the developer is aware of the algorithms used to determine the true angle and the measured angle, and is best able to determine and compensate for the errors introduced by the particular gaze tracking technique employed. Additionally, in the example of a gaze tracking device used to determine where, on a displayed image, the user is gazing, the angle-correction function must be applied before the coordinates of the gaze point on the display are determined.

Developers of applications that use the results provided by a gaze tracking device often desire to make their applications compatible with a variety of gaze tracking devices, to give their applications a broader market appeal. Preferably, these applications should provide the same functional utility regardless of the characteristics of the different gaze tracking devices. In like manner, the application should provide the same functional utility regardless of the size of the display being used (within practical limits).

If different gaze tracking devices exhibit different levels of accuracy or precision, the application developer must either design the application to be compatible with the device having the poorest accuracy, which may limit the functionality of the application, or must work with the provider of the poorest gaze tracking device to enhance the inherent accuracy of this gaze tracking device.

In addition to differing accuracy characteristics, different gaze tracking devices will also exhibit differences in other performance factors, such as 'noise' or 'jitter' caused by factors such as actual minute movements of the eye while gazing at a target, variances inherent in the algorithms used to compute the gaze angle, variances in the signals provided by the sensors used to detect the gaze angle, and so on. Depending upon the particular gaze tracking device, the device may provide 'raw' data corresponding to each determination of each coordinate on the display, or 'smoothed' data corresponding, for example, to a running average of the determined coordinates. A stream of raw data necessitates a smoothing algorithm in the application, whereas smoothed data introduces a lag in the responsiveness of the gaze tracking device.

SUMMARY OF THE INVENTION

It would be advantageous to provide a calibration method and system for gaze tracking that is not based on the assumption that the errors associated with a measured gaze of a user exhibits a uniform behavior across a user's field of view. It would also be advantageous to provide a gaze tracking system that is substantially independent of the technology used to provide the gaze point coordinates on a display. It would also be advantageous to provide a gaze tracking system with improved accuracy, based on this calibration method. It would also be advantageous to provide improved noise reduction (smoothing) based on this calibration.

To better address one or more of these concerns, in an embodiment of this invention, 'localized' error correction may be applied. The display area may be partitioned into error-correction zones, and each zone may have its own error correcting parameters or function. Calibration points may be defined for each of these zones, and the correction parameters or function within each zone may be dependent upon the observed errors as the user views each calibration point associated with the zone. In like manner, the function applied to smooth the determined gaze point to reduce noise may also be localized by basing its characteristics on the noise exhibited at each calibration point associated with defined noise-calibration zones. The error correcting function and/or the noise smoothing function may be selected based on the requirements of the particular application that receives the corrected and smoothed gaze location.

An example embodiment of a gaze-tracking system of this invention may include a gaze tracking device that identifies a location on a display area based on a gaze of a user, a gaze calibration element that determines a correction factor for each of a plurality of calibration points associated with zones of the display area, and a gaze correction element that provides a corrected location to an application based on the determined correction factors.

An example gaze calibration element defines a pattern of calibration points on the display area, and, for each calibration point: illuminates the calibration location, receives reported locations on the display area as the user gazes at the illuminated calibration point, and determines an offset error associated with the calibration points, based on a difference between the reported locations and the calibration point. Thereafter, the calibration element determines a correction offset for each calibration point based on these offset location errors at the one or more calibration locations.

An example gaze correction element subsequently receives a reported gaze location on the display from the gaze tracking device, determines a zone corresponding to the reported gaze location, and applies a correction function of this zone, based on the correction offsets of each calibration point associated with the zone, to determine a correction offset that may be applied to the reported gaze location to determine a corrected location. This corrected location is communicated to an application that uses the corrected location to perform a function that is dependent upon the corrected gaze location.

In like manner, the display area may be partitioned into noise-correction zones, and the smoothing function that is applied to reduce the noise associated with the determined gaze location may also be dependent upon which noise-correction zone the reported gaze location is situated.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions. The drawings are included for illustrative purposes and are not intended to limit the scope of the invention.

DETAILED DESCRIPTION

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the Figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

Figure 2:
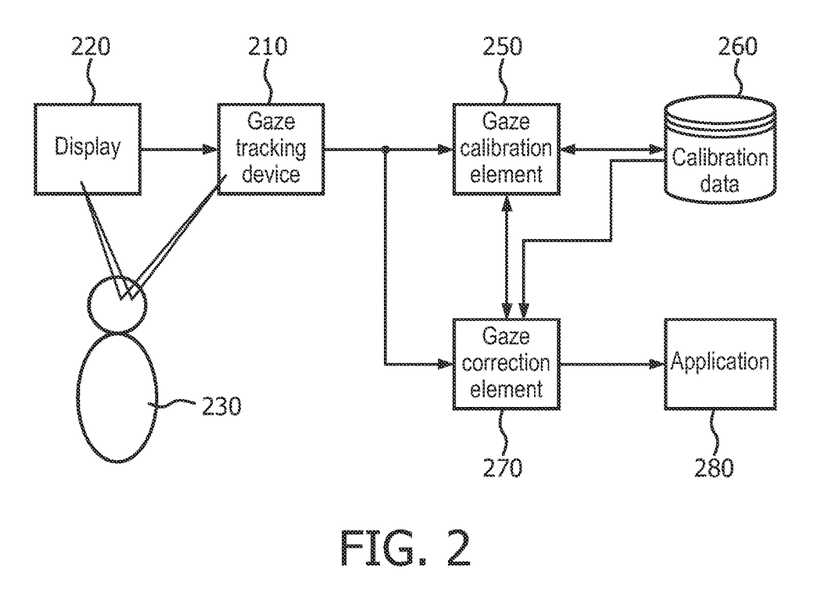
FIG. 2 illustrates an example gaze tracking system in accordance with aspects of this invention.

In an example embodiment of this invention, a conventional gaze tracking device 210 is used to provide coordinates corresponding to a location on a display area 220 where the gaze tracking device 210 determines the user 230 is gazing. The gaze tracking device 210 is fully configured to report coordinates on the display area 220 corresponding to the user's current gazing direction. That is, any calibration that is required by the particular device 210 for reporting gaze coordinates as the user 230 gazes the display area 220 has been performed. If such calibration is optional for using the device 210 to report gaze coordinates, it is also optional for use in this invention.

A calibration element 250 is configured to provide one or more error correcting functions 260 that are intended to correct the reported location, based on the below described calibration process. As used hereinafter, the term 'correction functions' includes functions having different forms, or functions having the same form but different parameters. For example, the correction functions may include linear and non-linear functions, or they may each be a common type of function, such as a linear function (x'=a+b*x), but with potentially different parameter values (offset, a, and slope, b).

A correction element 270 is configured to apply at least one of these error correcting functions 260 to the reported location to produce a corrected location that may be used by an application 280 that uses gaze-based locations on the display area 220 to perform a given function.

Figure 3:
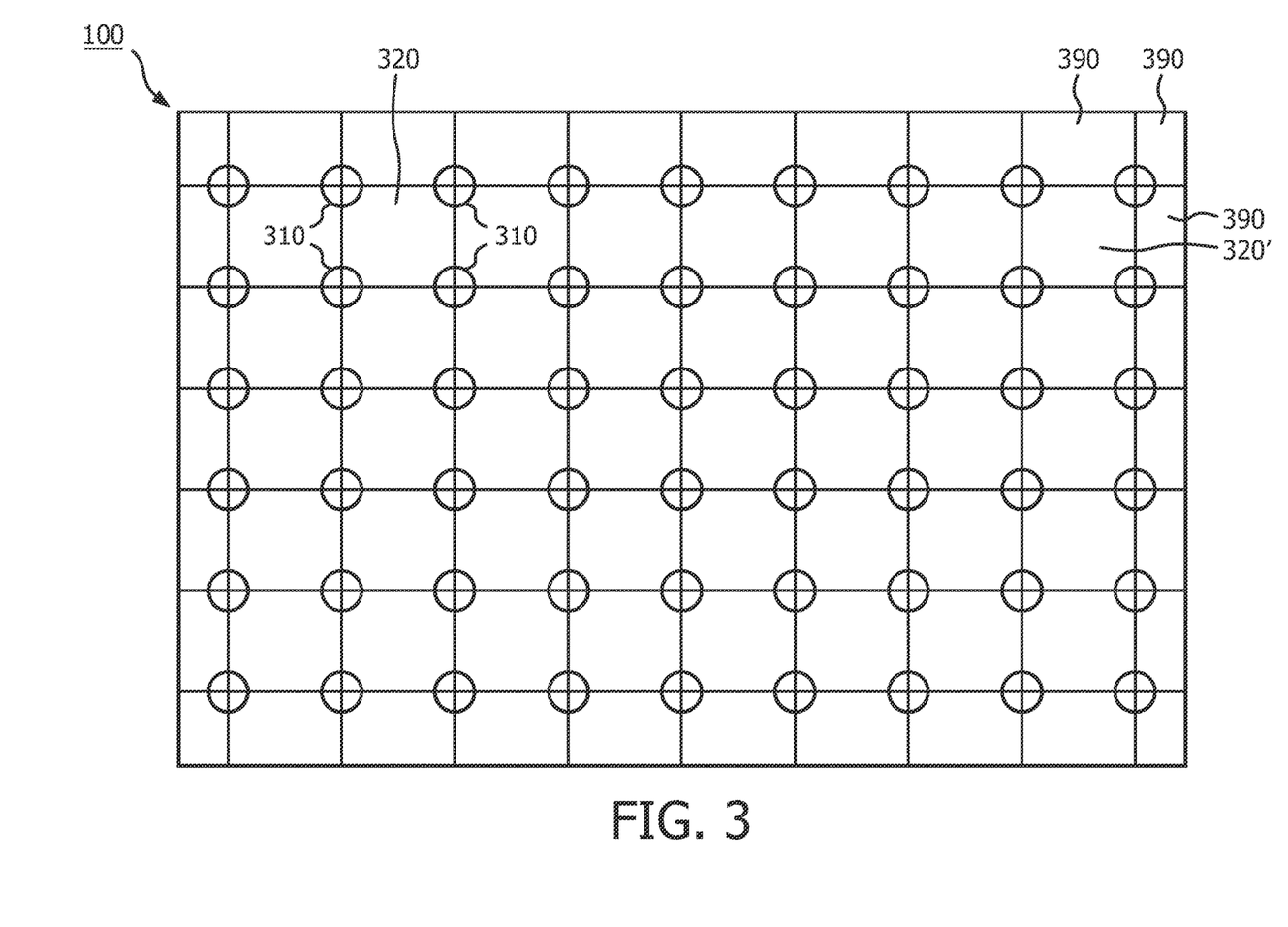
FIG. 3 illustrates a set of example calibration locations on a display that are associated with defined zones of the display.

As illustrated in FIG. 3, the display area 100 at which the user will be gazing may be partitioned into zones 320, each zone 320 including at least one calibration location 310. The calibration locations 310 may be used to define each zone 320, or the zones 320 may be used to define the calibration locations 310. Generally, the number and size of the zones 320 will be dependent upon a desired degree of accuracy and resolution, the size of the display area, and the expected accuracy from the gaze tracking device.

In FIG. 3, the calibration points 310 are the vertices of each rectangular zone 320. As detailed further below, other arrangements of calibration points and zones may be used. For example, using the calibration points 310 of FIG. 3, an alternative partitioning of the display area 100 could be a rectangular zone centered on each of the calibration points 310.

The pattern of calibration points 310, and in particular the number of calibration points and zones may be predefined, or it may be user definable. In some embodiments, the provider of the particular application 280 may specify a given accuracy and resolution, and the calibration element 350 may be configured to select an appropriate pattern of calibration points 310 to satisfy these requirements given the particular characteristics of the gaze tracking device 210, the size of the display 220, and/or other factors.

In an embodiment of this invention, the calibration element 250 of FIG. 2 may be configured to sequentially distinguish each calibration point 310, for example by sequentially illuminating each of the calibration points 310, or, equivalently, illuminating an area of the display that is centered on the calibration point 310, such as the illustrated white circles surrounding each calibration point 310.

The illumination may be for a fixed duration, within which the calibration element 250 receives the determined coordinates of the user's gaze on the display area 100 (hereinafter the gaze point, or gaze coordinates) from the gaze tracking device 210. The calibration element 250 may ignore the initially reported coordinates for the next calibration point as the user changes from the prior illuminated calibration point 310.

The calibration element 250 may also provide an audible signal when the recording of gaze points for an illuminated calibration point is completed and the calibration point is changing, then again when it begins to record the reported gaze coordinates corresponding to the newly illuminated calibration point 310.

Alternatively, the user may use a trigger, such as a mouse click, to inform the calibration element 250 that the user is currently gazing at the illuminated calibration point, and the calibration element 250 may commence recording of the reported gaze points.

In some embodiments, all of the calibration points may be illuminated, and the user sequentially gazes at each of the calibration points, then notifies the calibration element 250 that all of the calibration points have been gazed at. The calibration element 250 may then use techniques to associate the recorded gaze points with each calibration point, such as clustering, and to ignore outliers that are likely the gaze points that were recorded while the user's gaze shifted from one calibration point to the next.

As detailed further below, after recording the reported gaze coordinates at each calibration point 310, the calibration element 250 may determine a single measured gaze coordinate corresponding to these reported gaze coordinates for each calibration point, and this single measured gaze coordinate may be compared to the known coordinates of the corresponding calibration point to determine an error factor associated with each calibration point.

Upon initiation of the recording of gaze coordinates for each calibration point, the calibration element 250 may record a predetermined number of reported gaze coordinates from the gaze tracking device 210. Alternatively, the calibration element 250 may be configured to continue to record the gaze coordinates until the variance among these reported coordinates indicates that a reliable determination of the measured gaze coordinate can be determined. That is, for example, if the user's gaze is steady, with little difference among the reported gaze coordinates, the recording may be terminated after only a few reported gaze coordinates are received. On the other hand, if the user's gaze is wandering or otherwise unsteady, with relatively larger differences among the reported gaze coordinates, the calibration element 250 may continue to record a larger number of reported gaze coordinates, providing a larger sample size for determining the single measured gaze coordinate for the calibration point.

In some embodiments, a combination of a predetermined number of samples and a variable number of samples may be used. For example, it may be determined that the typical user is able to maintain a steady focus on calibration points near the center of the display area 100, and tend to exhibit less of an ability to focus on calibration points around the periphery of the display area 100, the calibration element 250 may be configured to collect a predetermined number of samples at calibration points near the center of the display 100, and larger predetermined number of samples as the distance of each calibration point from the center of the display 100 increases.

Figure 4:
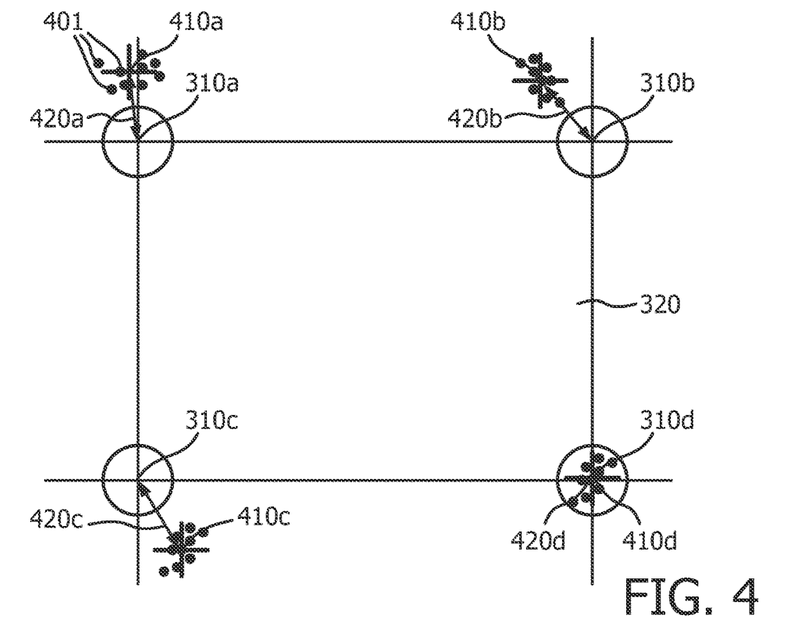
FIG. 4 illustrates an example set of reported gaze locations as a user gazes at each of a set of calibration locations.

FIG. 4 illustrates an example set of measured gaze locations 410a-410d as a user gazes at each calibration location 310a-310d. Individual reported gaze points 401 about each calibration location 410a-410d are illustrated. These gaze points 401 are situated at a determinable distance from their corresponding calibration location 410a-410d, and this distance corresponds to an error of each reported gaze point 401 from the gaze tracking device 210. The calibration element 250 processes these gaze points 401 to determine a single measured gaze location 410a-410d at each corresponding calibration point 310a-310d. In an example embodiment the measured gaze location 410a-410d for each calibration point 310a-310d may be a location that minimizes the sum of the squares of errors of each reported gaze location 401 associated with the calibration point 310a-310d, using techniques common in the art. Other techniques may be used to determine a single measured gaze location corresponding to each set of gaze locations associated with each calibration point may be used as well.

This example set of reported gaze locations 410a-410d illustrates a non-uniform, and non-linear set of location errors, or offsets 420a-420d between the measured gaze locations 410a-410d and the true locations of the calibration points 310a-310d. The particular gaze tracking device 210 used by the particular user 230 for reporting gaze locations on the particular display 220 exhibits an offset 420a that is slightly to the left and substantially above the calibration point 310a; an offset 420b that is substantially to the left and above the calibration point 310b; an offset 420c that is substantially to the right and below the calibration point 310c; and a negligible offset 420d (not illustrated, per se) with respect to calibration point 310d.

Each of these offsets, Oa(x,y) 420a, Ob(x,y) 420b, Oc(x,y) 420c, and Od(x,y) 420d are recorded for each calibration point 310a-310d respectively. The above process is applied to each of the N calibration points, providing offsets $O_1(x,y)$, $O_2(x,y)$, ... $O_N(x,y)$ associated with each of the N calibration points. In the example of FIG. 3, FIG. 3, N=54 (9×6) calibration points.

It is significant to note that each zone 320 of FIG. 3 is associated with a different set of calibration points 310, and thus associated with a different set of calibration offset values. As detailed further below, the particular set of calibration offset values associated with a given zone define the parameters of the particular correction function that will be applied to subsequently reported gaze coordinates from the gaze tracking device 210.

The location of each calibration point 310 and its corresponding offset value may be provided to the gaze correction element 270. Alternatively, and particularly if the gaze calibration element 250 and the correction element 270 are within a common module, the gaze correction element 270 may be configured to access this data 260 via calls to the gaze calibration element 250, or via access to the same memory used by the calibration element 250 to store this data 260.

Figure 5:
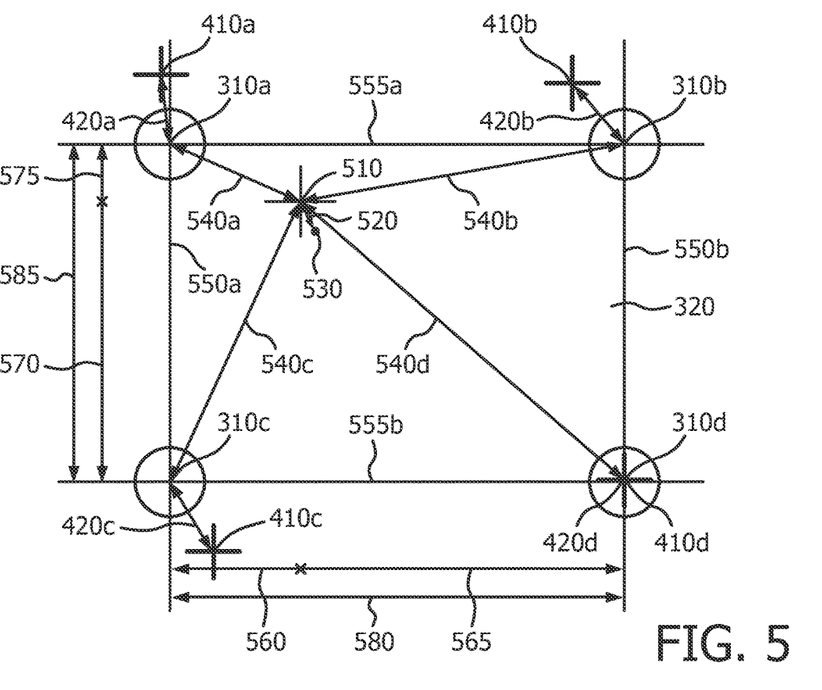
FIG. 5 illustrates an example correction of a reported gaze location based on the errors associated with each calibration point associated with a zone.

FIG. 5 illustrates an example correction of a reported gaze location 510 based on the errors (offsets) 420a-d associated with each calibration point 310a-d associated with a zone 320. In this example, the calibration points 310a-d define the four vertices of rectangular zone 320. When the reported gaze location 510 is received by the gaze correction element 270, the gaze correction element 270 determines which zone the gaze location 510 lies, then uses the location of the calibration points associated with the zone and their corresponding offsets to determine an appropriate correction offset to apply to the gaze location 510 to provide a corrected gaze location 520.

The gaze location 510 is closest to calibration point 310a, and furthest from calibration point 310d; accordingly, the correction 520 that may be applied to the gaze location 510 to produce a corrected location 530 may be more strongly influenced by the offset 420a associated with calibration point 310a. In like manner, the gaze location 510 is closer to the upper pair of calibration points 310a-310b than the lower pair of calibration points 310c, 310d, and the vertical correction of the gaze location 510 may be more strongly influenced by the offsets 420a, 420b associated with the upper pair of calibration points 310a, 310b.

Any number of techniques, such as multivariate interpolation and others, may be used to determine a correction offset 520 that reflects the influence of each of the calibration offsets 420a-420d (the offset 420d in this example is negligible and not illustrated, per se) based on the location of the gaze location 510 relative to the calibration points 310a-310d.

In an example embodiment, a multivariate interpolation is based on "distance weighting", wherein the correction offset is based on the distance 540a-540d between the gaze point 510 and each of the calibration points 310a-310b, the distances defining a weight that indicates the influence that the offset 420a-420d of each calibration point 310a-310d may have on the determined correction offset 520, where less weight is given to more distant calibration points.

Let Pg represent gaze point 510, Ca, Cb, Cc, and Cd represent the calibration points 310a-310d, Da, Db, Dc, and Dd represent the distances 540a-d, normalized by the diagonal distance between diagonally situated calibration points (i.e. distance between Ca and Cd, or between Cb and Cc). Let Oa, Ob, Oc, and Od represent the offsets 420a-420d. The weight of each offset Oa, Ob, Oc, and Od may be defined as (1-Da), (1-Db), (1-Dc) and (1-Dd), respectively.

The offset Op 520 that may be applied to gaze point Pg 510 may be defined as:

Op=(1-Da)*Oa+(1-Db)*Ob+(1-Dc)*Oc+(1-Dd)*Od.

An advantage of this technique is that it can be applied to an arbitrarily situated set of calibration points, provided suitable normalization is applied (sum of weights equals 1.0). In like manner, this technique can be applied to zones defined by more or fewer calibration points than the four used in FIG. 3. In some embodiment, a zone may include calibration points within the zone as well as on the perimeter of the zone, for example, a zone may comprise a 3×3 arrangement of calibration points, with a central calibration point and eight calibration points along its perimeter.

Another common multivariate interpolation technique is a bilinear interpolation, wherein a linear interpolation along each edge 550a, 550b is applied to determine a first offset of the gaze point 510, then applied along each edge 555a, 555b to determine a second offset, using the values of the first offset. This second offset is the correction offset 520 that may be applied to the gaze location 510 to produce a corrected offset 530. The interpolation process may be applied in reverse order; i.e. interpolate along edges 555a, 555b to produce the first offset, then interpolate along edges 550a, 550b using the values of the first offset to achieve the same correction offset. This result is similar to the above distance interpolation, except that the weights are based on the product (Dh*Dv of the horizontal distance Dh 560, 565 and the vertical distance Dv 570, 575 from the gaze location 510 to each calibration point 310a-310d, normalized by the product (DH*DV) of the width DH 580 and the height DV 585 of the zone 320. This technique avoids needing to explicitly determine the vector distance from the gaze point 510 to each calibration point 310a-310d.

Other multivariate interpolation techniques, common in the art, may be used, including Barnes interpolation, Bicubic interpolation, Inverse distance weighting, Natural neighbor interpolation, and others.

One of skill in the art will recognize that an interpolation may be performed for points that are not within the perimeter of the arrangement of calibration points. For example, the areas 390 beyond the extent of the calibration points may be considered to be included in the zone 320' that is adjacent to these areas 390.

In another example embodiment, machine learning techniques may be used to determine the correction offset within each zone based on a set of calibration points associated with the zone. For example, an artificial neural network for the zone may be trained using the reported gaze points 401 collected for each of the calibration points 310a-310d associated with the zone 320. After training the neural network, the subsequently reported gaze position 510 from the gaze tracking device 210 is received, the zone 320 corresponding to the reported gaze position 510 is determined, and the neural network that has been trained for this zone 320 is provided the reported gaze position 510 as an input, and the output of the neural network is the corrected gaze coordinate 530.

Depending upon the desired accuracy and precision, more complex or less complex techniques may be used to provide corrected coordinates. For example, in a straightforward embodiment, the correction offset may merely be the offset of the closest calibration point ("nearest neighbor" interpolation). In such an embodiment, rectangular zones are formed, centered on the calibration point, and determining the zone of the gaze point 510 determines the offset 420 to be applied to the gaze position 510. This technique is particularly well suited for an application 280 with specifically situated buttons that are selectable by gazing at the button. The zones will correspond to the individual buttons, and the calibration point will be at the center of each button, and different sized buttons will produce different sized zones. In some embodiments, the gaze correction element 270 may also provide an 'alert' to the application 280 when the corrected gaze point 520 is near the boundary between two adjacent buttons, thereby providing a 'guard zone' around the perimeter of each button.

Figure 6:
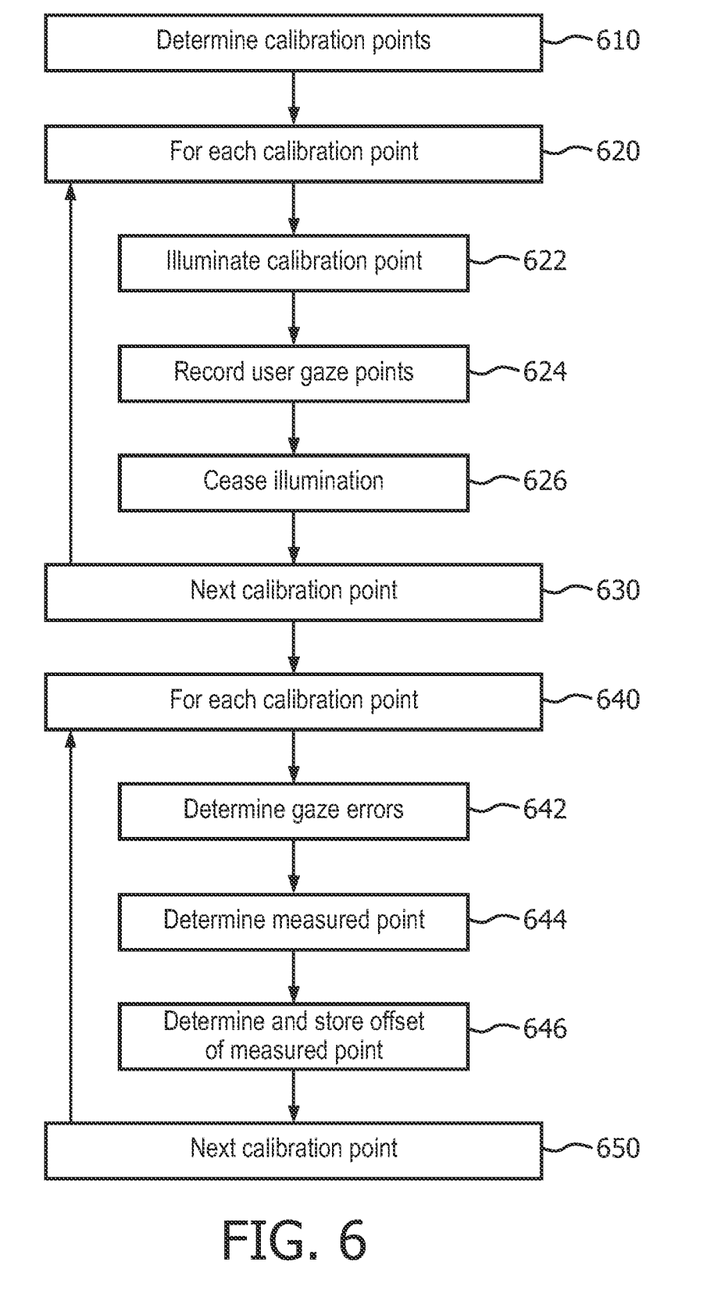
FIG. 6 illustrates an example flow diagram for determining offsets for calibration points.

FIG. 6 illustrates an example flow diagrams for determining offsets for calibration points.

At 610, the pattern of calibration points is determined. The number and placement of the calibration points may be dependent upon the requirements of the target application that will receive the corrected gaze point, as discussed above.

The loop 620-630 is executed for each calibration point. At 622, the calibration point is illuminated, the user having been instructed to gaze at each illuminated point. At 624, the gaze tracking device provides gaze points corresponding to the point on a display at which the user is gazing. A number of these gaze points are recorded, as detailed above, the illumination ceases 626, and the process repeats for the next calibration point, at 630.

After the gaze points are collected for each calibration point, these gaze points of each calibration point are processed in the loop 640-650 to determine a calibration offset for each calibration point.

At 642, the gaze error associated with each recorded gaze point corresponding to the calibration point is determined, based on a distance between the recorded gaze point and the location of the calibration point.

At 644, a measured point corresponding to a composite of the recorded gaze points for the calibration point is determined, based on the determined errors. As noted above, this measured point may be a location that minimizes the sum of the square error of each gaze point, although other techniques may be applied to determine the measured point.

At 646, the offset of the measured point from the calibration point is determined and stored as the offset associated with this calibration point, and the process is repeated 650 until the offset for each of the calibration points is determined.

One of skill in the art will recognize that the two loops 220-230 and 240-250 could be combined as a single loop 220-250, wherein the offset associated with a calibration point is determined before the next calibration point is illuminated.

Figure 7:
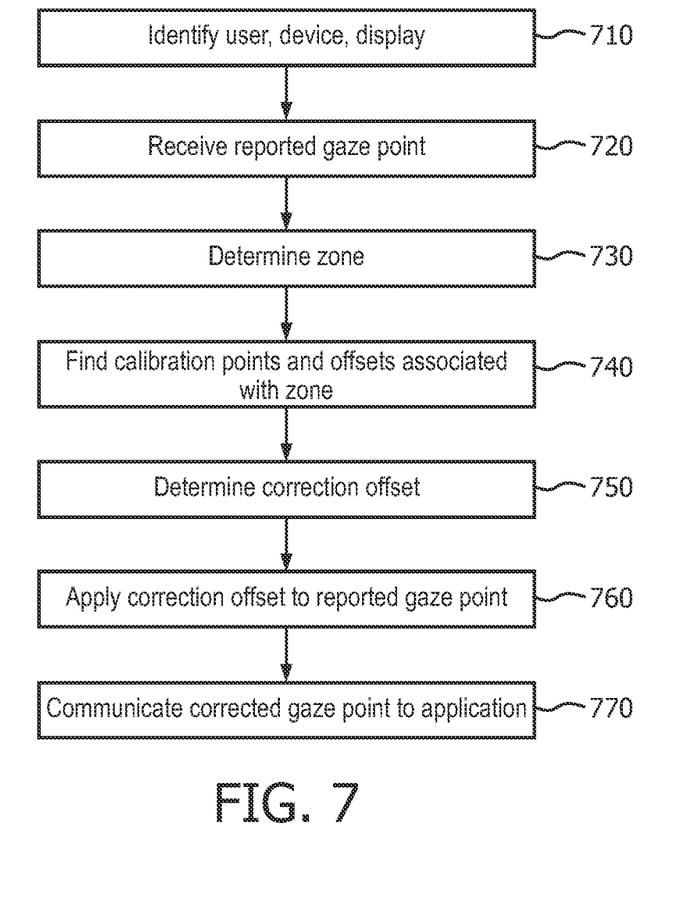
FIG. 7 illustrates an example flow diagram for correcting reported gaze coordinates based on these offsets.

FIG. 7 illustrates an example flow diagram for correcting gaze points that are provided by a gaze tracking device after the calibration process of FIG. 6 is completed.

At 710, assuming that a number of different sets of calibration data are accessible by the gaze correcting element, the process identifies the user, the gaze tracking device, and the display, so that the calibration data corresponding to this arrangement can be accessed. If the user's gaze has not been calibrated using the given gaze tracking device and display (or their equivalents), the user may be instructed to perform this calibration prior to using the gaze correction element.

At 720, the current gaze point of the user is received from the gaze tracking device, and at 730, the zone in which the current gaze point is located is identified. It is significant to note that the correction element may define zones differently from the assumed zones used in the calibration process. That is, although the calibration points may have been arranged to provide a particular partitioning of the display area, that partitioning is independent of the partitioning that the correction element may select.

At 740, the location and offset of each calibration point related to the determined zone of the gaze point are obtained. As noted above, the gaze calibration element may store the locations and offsets in a memory that is accessible by the gaze correction element, or it may provide this information in response to a request from the gaze correction element.

At 750, the correction offset that is to be applied to the gaze point is determined. As noted above, any of a variety of techniques may be applied to determine this offset based on the offsets associated with the calibration points of the zone.

In some embodiments, the gaze correction element may be configured to include a plurality of correction techniques, and configured to enable the selection of a particular correction technique, typically depending upon the needs of the application that will be using the corrected gaze point. As noted above, an application that only needs to determine which 'button' on the display is being gazed at would be accommodated by a 'nearest neighbor' interpolation. The selection of the correction technique may also be dependent upon the pattern of calibration points, because some correction techniques may place constraints on the arrangement of points used by the technique. In some embodiments, the gaze correction element may be configured to select a 'default' correction technique based on the given pattern of calibration points, particularly if there is a 'better' (faster, more accurate, etc.) technique available because of the given pattern.

As noted above, a machine learning element may be trained to produce corrected coordinates, without the intermediate step of identifying an offset. However, the process effectively determines an offset in order to transform the input gaze point to a corrected gaze point that is offset from the gaze point by a given amount.

At 760 the determined offset is applied to the input gaze point, and the corrected gaze point is communicated to the application at 770. Any of a variety of techniques may be used to communicate the corrected gaze point to the application, commonly distinguished as "push" techniques, wherein the correction element continually, or nearly continually, transmits the corrected gaze point to the application, and "pull" techniques, wherein the application requests the corrected gaze point and the correction element provides it. In some embodiments, the correction element may be configured to continually update a memory location, or locations (e.g. circular buffer), and the application is configured to access this memory whenever it needs the most recent corrected gaze point(s).

As noted above, localized smoothing functions may be applied to mitigate the noise associated with determining a user's gaze point. Such noise may be actual changes in the user's gaze as the user gazes at a given target, or it may be noise associated with the sensors used to detect the user's gaze, or other factors. In some embodiments of this invention, a noise calibration process is applied to determine the function that best smooths a sequence of reported gaze points for each of a plurality of noise zones. This function is subsequently applied to sequences of reported gaze points when the user is gazing within the particular noise calibration zone.

In an example embodiment, a noise calibration element is included in the gaze calibration element 250 of FIG. 2, and a noise smoothing element is included in the gaze correction element 270. In the example embodiment detailed below each of these noise elements receive error-corrected gaze points from the offset correction element in the gaze correction element, and the output of the gaze correction element 270 that is provided to the application 280 is a smoothed error-corrected gaze point. Other configurations will be evident to one of ordinary skill in the art in view of this disclosure.

Figure 8:
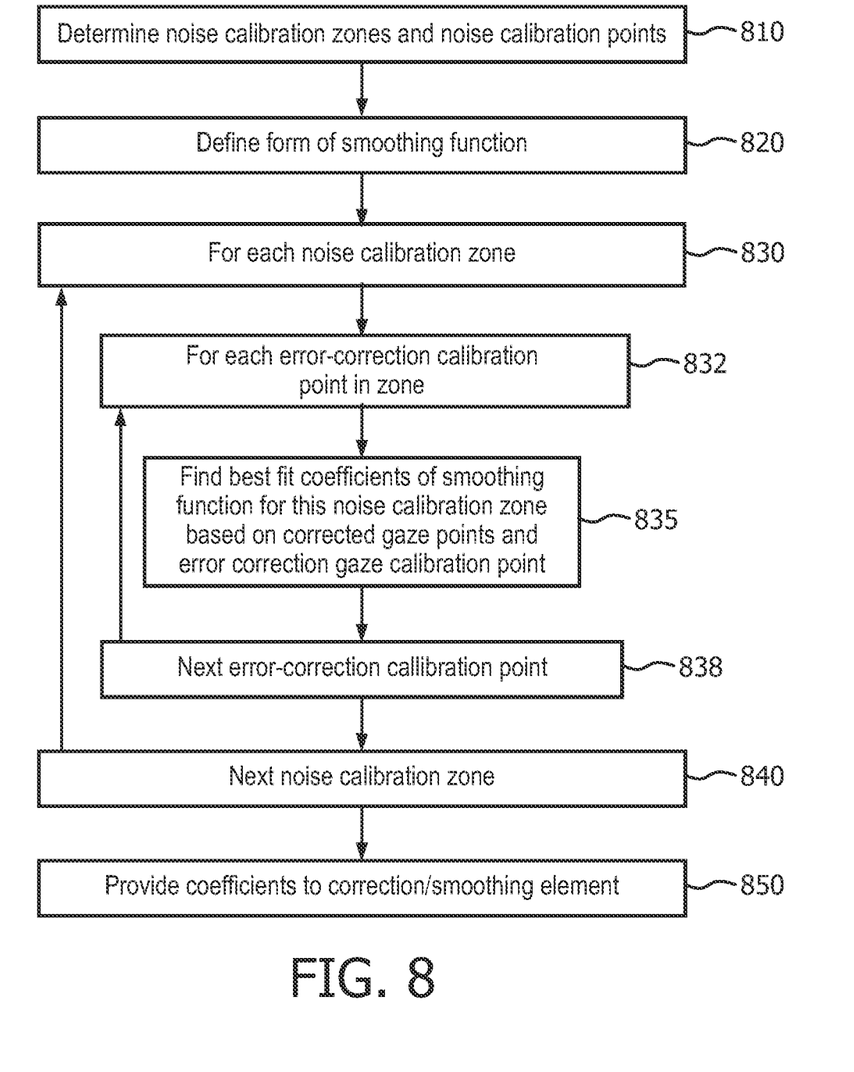
FIG. 8 illustrates an example flow diagram for determining noise smoothing functions for noise calibration zones.

FIG. 8 illustrates an example flow diagram for determining noise smoothing functions for noise calibration zones.

At 810, the noise calibration zones are defined, with corresponding noise calibration points. These noise calibration zones and noise calibration points may correspond to the error-correcting zones 320 and calibration points 310, or they may be different. For example, the noise calibration zones may include a center area of the display, surrounded by other noise calibration zones, such as provided by an N×N set of noise calibration zones, where N is an odd integer.

The noise calibration points may be the same as the error-correcting calibration points 310, avoiding the need to perform a separate noise calibration exercise. The noise calibration zone may be associated with only one of the error-correction calibration points 310, such as a calibration point 310 near the center of the defined noise calibration zone; or it may be associated with all of the error-correction calibration points 310 within its zone; or any other meaningful selection.

At 820, the form of the smoothing function is defined. Conventional smoothing functions often use a weighted average of the past M reported gaze points, wherein the weights are higher for more recently reported gaze points, and lower for older points. The choice of M and the particular weights used define the shape of the filtering/smoothing function. A large value of M introduces a lag in providing the smoothed gaze point, because it requires all of the M gaze points to be collected before the smoothed gaze point can be provided. The 'slope' of the weights determine the responsiveness of the system as the user changes gaze points; if the older gaze points have significant weight, the smoothed gaze point will be located somewhere between the new gaze point and the old gaze point, and will 'catch up' to the new gaze point when all of the M points are collected while the user is gazing at the new gaze point.

In an example embodiment, the form of the smoothing function may be a weighted average wherein the weights (coefficients) applied to each of the prior gaze points may be individually determined for each noise calibration zone. In other embodiments, the smoothing function may be a polynomial that is curve-fit to best match the calibration gaze points to the smoothed gaze points. Other means of determining parameters of a function that best matches the calibration gaze points to the determined smoothed gaze point will be evident to one of skill in the art.

Of particular note, the smoothing function may be embodied in a machine learning element, such as an artificial neural network, as detailed further below.

The loop 830-840 determines the smoothing function for each noise calibration zone; in this example embodiment the form of the smoothing function is the same within each zone, and the task is to find the particular coefficients of the function within each noise smoothing zone. In other embodiments, different forms of the smoothing function may be defined for the different noise smoothing zones.

All of the error-correction calibration points associated with each zone are processed in the loop 832-838, to determine the coefficients (or other parameters) of the smoothing function that best fits each resultant smoothed gaze point to the calibration point, at 835. A minimum-sum-of-square-errors technique is commonly used to define such a best fit set of coefficients. In an example embodiment, the corrected gaze points from the error-correction element are used to determine the errors of the smoothed gaze points with respect to the location of each calibration point on the display.

If a machine learning element is used, the M error-corrected points are provided as the input to the machine learning element during the training stage, with the location of the corresponding error-correction calibration point as the desired/correct output. As each set of M error-corrected points are provided for the given noise calibration zone, the machine learning element will adjust its internal parameters (e.g. weights associated with nodes within a neural network) to provide an output that best matches the desired/correct output.

At 850, the noise smoothing coefficients for each noise calibration zone, or the trained machine learning element, is provided to the element in the gaze correction system that smooths the corrected gaze points. As with the offsets provided for each error-correction zone, the communication of these noise calibration parameters to the noise smoothing element may be accomplished by an explicit transmission of these parameters, or by storing these parameters in a memory that is accessible to the noise smoothing element.

In another example embodiment of this invention, the value of M may be dynamically determined for each noise calibration zone. That is, for example, the smoothing function of a particular noise calibration zone may first be defined having a low value of M, such as three. The best-fit parameters of the smoothing function may be determined using this low value of M for all of the corrected gaze points available for the associated calibration points in this particular noise calibration zone, or the machine learning element may be trained using M corrected gaze points as input, and the variance of the differences between each smoothed gaze point and its corresponding calibration point may be determined. If the variance is below a given threshold, this value of M may be used for the smoothing function associated with this particular zone. If the variance is above this threshold, the value of M is increased and the process is repeated until either the determined variance is below the threshold, or a maximum value of M is reached. In this manner, for example, fewer smoothing points may be required in the center of the display area than at the periphery of the display area, providing a more rapid response time when gazing near the center of the display.

Figure 9:
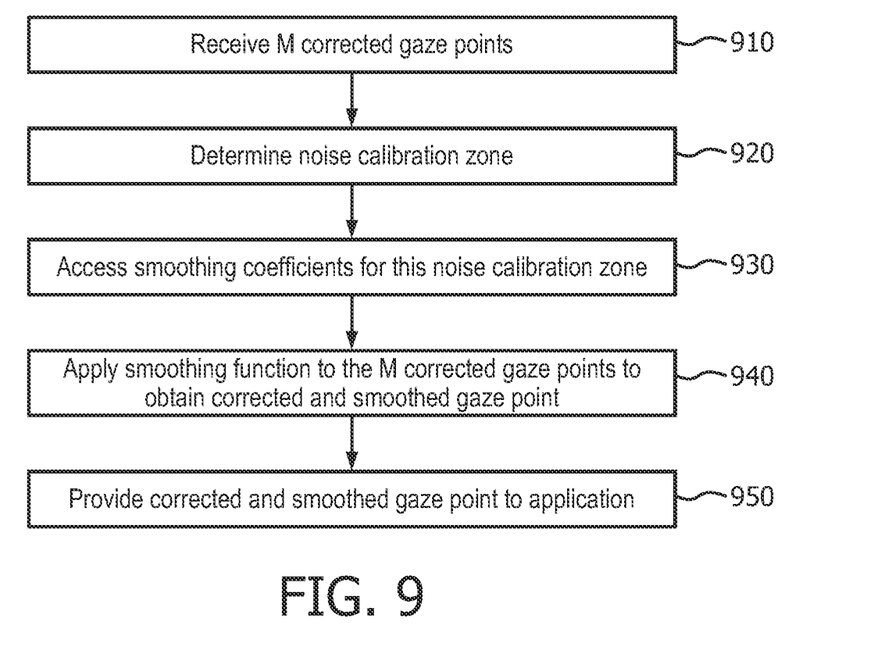
FIG. 9 illustrates an example flow diagram for smoothing corrected gaze coordinates based on these noise smoothing functions.

FIG. 9 illustrates an example flow diagram for smoothing corrected gaze coordinates based on the aforementioned noise smoothing functions.

In this example embodiment, the smoothing function is defined based on receiving M corrected gaze points, at 910, where M is the same in all noise calibration zones; if M varies based on the particular noise calibration zone, the order of steps 910 and 920 may be reversed.

At 920, the noise calibration zone is determined, typically based on the most recently received corrected gaze point. The determined noise smoothing parameters for this noise calibration zone are accessed, at 930, and the smoothing function with these parameters, or the trained machine-learning element for this zone, is applied to the M most recent corrected gaze points, at 940.

The smoothed corrected gaze point is then communicated to the application, at 950, either via an explicit communication, or via access to a common memory.

While the invention has been illustrated and described in detail in the drawings and foregoing description, such illustration and description are to be considered illustrative or exemplary and not restrictive; the invention is not limited to the disclosed embodiments.

For example, although a symmetric rectilinear arrangement of calibration points are illustrated in FIGS. 3-5, one of skill in the art will recognize that it is possible to operate the invention in an embodiment wherein other arrangements are feasible. For example, the calibration points may be denser toward the perimeter of the display, and less dense near the center of the display. In some embodiment, the calibration points may be the vertices of 'tiled' triangles, or other polygons arranged in a regular pattern (equal sized zones) or semiregular pattern (groups of unequal sized zones arranged in a regular pattern). In some embodiments, the pattern of calibration points may correspond to "Padua points", which are known to be optimal for total degree polynomial interpolation in two variables.

In like manner, although the examples indicate that the calibration points should be selectively 'illuminated', one of skill in the art will recognize that any of a variety of techniques may be used to distinguish the calibration point that the user is to gaze at during the calibration process. For example, the background of the display may be white, and the calibration point is turned off, creating a black point. In like manner the shape of the calibration points may distinguish the calibration point that the user is to gaze at.

Similarly, although a specific calibration process that is applied before operation in the application is disclosed, one of skill in the art will recognize that a dynamic calibration process may be applied after the application is in use. For example, the application may provide feedback that indicates when a user selects a particular 'button' on the display and proceeds in the application with the understanding that the button selected was the button that the user intended to select. A dynamic calibration process may interpret the coordinates of the selected button as a calibration location, then retrieve a number of the reported gaze locations contemporaneous with this button selection to determine and/or refine either the offset correction and/or the noise smoothing parameters.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system comprising:
a gaze tracking device;
a gaze calibration element;
a gaze correction element;
a noise calibration element; and
a noise smoothing element;
wherein:
the gaze calibration element is configured to define a plurality of calibration locations on a display area, and for each calibration location:
receive, from the gaze tracking device, one or more reported locations on the display area as a user gazes at the calibration location,
determine a location error associated with the calibration location, based on a difference between the one or more reported locations and the calibration location; and
the gaze correction element is configured to:
divide the display area into a plurality of correction zones, each correction zone including one or more of the plurality of calibration locations; and
for each correction zone: determine a correction function for the zone based on the location errors at the one or more calibration locations of the zone;
receive a subsequent gaze location provided by the gaze tracking device,
determine a particular zone based on the subsequent gaze location, and
apply the correction function of the particular zone to the subsequent gaze location to determine a corrected location;
the noise calibration element is configured to:
divide the display area into a plurality of noise calibration zones, each noise calibration zone including one or more noise calibration locations; and
for each noise calibration zone: determine coefficients of a smoothing function for the noise calibration zone, based on a plurality of corrected gaze locations from the gaze correction element while a user gazes at each noise calibration location; and
the noise smoothing element is configured to:
receive a plurality of subsequent corrected gaze locations from the gaze correction element,
determine a particular noise calibration zone based on at least one of the subsequent corrected gaze locations,
apply the smoothing function of the particular noise calibration zone to the plurality of subsequent corrected gaze locations to determine a smoothed gaze location, and
communicate the smoothed gaze location to an application.

2. The system of claim 1, wherein the correction function for a first zone of the plurality of correction zones differs from the correction function for a second zone of the plurality of correction zones.

3. The system of claim 1, wherein the gaze calibration element is configured to distinguish each of the calibration locations on the display to facilitate the user's gazing at the calibration location.

4. The system of claim 1, wherein the gaze calibration element is configured to terminate receiving reported locations for each calibration location after a select number of reported locations are received for the calibration location, and the select number is based on a variance among the reported locations.

5. The system of claim 1, wherein the gaze calibration element is configured to determine the location error for at least one of the calibration locations based on a least-square error technique.

6. The system of claim 1, wherein the gaze correction element is configured to determine the corrected location in at least one of the calibration zones based on a vector distance between the subsequent gaze location and each of the calibration locations of the particular zone.

7. The system of claim 1, wherein the gaze correction element is configured to determine the corrected location in at least one of the calibration zones via a bilinear interpolation based on the subsequent gaze location and the location errors of the calibration locations of the particular zone.

8. The system of claim 1, wherein the gaze calibration element is configured to determine the correction function by training a learning machine based on the reported locations and the calibration locations, and the gaze correction element determines the corrected location by applying the subsequent gaze location to the learning machine.

9. The system of claim 1, wherein the gaze correction element is configured to determine the corrected location as the calibration location that is closest to the subsequent gaze location.

10. The system of claim 1, wherein the gaze correction element includes more than one correction function for at least one of the correction zones, and is configured to select the correction function that is used to correct the subsequent gaze location based on one or more requirements of the application.

11. The system of claim 1, wherein the noise calibration locations correspond to the calibration locations.

12. A gaze-tracking system comprising:
a gaze tracking device configured to identify a location on a display area based on a gaze of a user, and
a noise smoothing element;
characterized in that the gaze-tracking system comprises a noise smoothing function calibration element, wherein the noise smoothing function calibration element is configured to:
divide the display area into a plurality of noise calibration zones, each noise calibration zone including one or more noise calibration locations; and
for each noise calibration zone:
determine coefficients of a smoothing function for the noise calibration zone, based on a plurality of gaze locations while a user gazes at each noise calibration location; and
the noise smoothing element is configured to:
receive a plurality of subsequent gaze locations,
determine a particular noise calibration zone based on at least one of the subsequent gaze locations,
apply the smoothing function of the particular noise calibration zone to the plurality of subsequent gaze locations to determine a smoothed gaze location, and
communicate the smoothed gaze location to an application.

13. The gaze-tracking system of claim 12, wherein the plurality of noise calibration zones includes an N×N array of rectangular noise calibration zones, where N is an odd integer.

14. The gaze-tracking system of claim 12, wherein the smoothing function of at least one noise calibration zone includes a weighted average of the plurality of subsequent gaze locations, and the noise calibration element defines weights for this weighted average based on the plurality of gaze locations.

15. A non-transitory computer-readable medium that includes a program that, when executed by a processing system, causes the processing system to:
divide a display area into a plurality of noise calibration zones, each noise calibration zone including one or more noise calibration locations; and
for each noise calibration zone: determine coefficients of a smoothing function for the noise calibration zone, based on a plurality of gaze locations received from a gaze tracking device while a user gazes at each noise calibration location,
receive, from the gaze tracking device, a plurality of subsequent gaze locations on a display area based on a subsequent gaze of a user,
determine a particular noise calibration zone based on at least one of the subsequent gaze locations,
apply the smoothing function of the particular noise calibration zone to the plurality of subsequent gaze locations to determine a smoothed gaze location, and
communicate the smoothed gaze location to an application.

16. The medium of claim 15, wherein the plurality of noise calibration zones includes an N×N array of noise calibration zones, where N is an odd integer.

17. The medium of claim 15, wherein the smoothing function of at least one noise calibration zone includes a weighted average of the plurality of subsequent gaze locations, and the noise calibration element defines weights for this weighted average based on the plurality of gaze locations.

18. The medium of claim 15, wherein the program causes the processing system to:
define a plurality of calibration locations, and for each calibration location:
receive, from the gaze tracking device, one or more reported locations on the display area as the user gazes at the calibration location,
determine a location error associated with the calibration location, based on a difference between the one or more reported locations and the calibration location; and
divide the display area into a plurality of correction zones, each correction zone including one or more of the plurality of calibration locations; and
for each correction zone: determine a correction function for the zone based on the location errors at the one or more calibration locations of the zone;
for each of the subsequent gaze locations received from the gaze tracking device:
determine a particular zone based on the subsequent gaze location, and
apply the correction function of the particular zone to the subsequent gaze location.

19. The medium of claim 18, wherein the program causes the processing system to:
   determine the correction function by training a learning machine based on the reported locations and the calibration locations, and
   applies the correction function to the subsequent gaze location by applying the subsequent gaze location to the learning machine.

20. The medium of claim 18, wherein the correction function comprises selection of the calibration location that is closest to the subsequent gaze location.

* * * * *